(12) United States Patent
    Ota

(10) Patent No.: US 10,094,935 B2
(45) Date of Patent: Oct. 9, 2018

(54) NUCLEAR MEDICINE EXAMINATION APPARATUS AND NUCLEAR MEDICINE EXAMINATION METHOD

(71) Applicant: DAI NIPPON PRINTING Co., Ltd., Tokyo (JP)

(72) Inventor: Kohei Ota, Tokyo (JP)

(73) Assignee: DAI NIPPON PRINTING Co., Ltd., Tokyo (JP)

( * ) Notice: Subject to any disclaimer, the term of this patent is extended or adjusted under 35 U.S.C. 154(b) by 0 days.

(21) Appl. No.: 15/935,142

(22) Filed: Mar. 26, 2018

(65) Prior Publication Data

US 2018/0246224 A1    Aug. 30, 2018

Related U.S. Application Data

(63) Continuation of application No. PCT/JP2016/078823, filed on Sep. 29, 2016.

(30) Foreign Application Priority Data

Sep. 30, 2015   (JP) .................................. 2015-193543

(51) Int. Cl.
    *G01T 1/161*   (2006.01)
    *A61B 6/00*    (2006.01)
    *A61B 6/03*    (2006.01)

(52) U.S. Cl.
    CPC .............. *G01T 1/161* (2013.01); *A61B 6/037* (2013.01); *A61B 6/481* (2013.01); *A61B 6/54* (2013.01)

(58) Field of Classification Search
    CPC ......... G01T 1/161; A61B 6/037; A61B 6/481; A61B 6/54
    See application file for complete search history.

(56) References Cited

U.S. PATENT DOCUMENTS 5,742,061 A * 4/1998 Lemonnier ............. H01J 47/06
                                                    250/374
6,822,239 B2 * 11/2004 Tanimori ................. G01T 1/185
                                                    250/385.1

(Continued)

FOREIGN PATENT DOCUMENTS

JP    3354551 B2    12/2002
JP    3535045 B2    6/2004

(Continued)

OTHER PUBLICATIONS

Written Opinion of the International Searching Authority for the PCT application No. PCT/JP2016/078823.

(Continued)

*Primary Examiner* — Marcus Taningco
*Assistant Examiner* — Djura Malevic
(74) *Attorney, Agent, or Firm* — TYPHA IP LLC

(57) ABSTRACT

A nuclear medicine examination apparatus is a nuclear medicine examination apparatus incorporating a Compton camera using gas amplification. The Compton camera has a chamber in which a gas is sealed. The nuclear medicine examination apparatus includes sensors that output signals each representing a gas state in the chamber and a controller that controls the gas state in the chamber on the basis of output signals from the sensors.

20 Claims, 12 Drawing Sheets

(56) References Cited

U.S. PATENT DOCUMENTS

| | | | |
|---|---|---|---|
| 7,170,066 B2* | 1/2007 | Virtanen | G01T 1/185 250/374 |
| 8,207,505 B2* | 6/2012 | Motomura | G01T 1/185 250/385.1 |
| 2002/0134945 A1 | 9/2002 | Tanimori et al. | |
| 2005/0006591 A1* | 1/2005 | Virtanen | G01T 1/185 250/374 |
| 2008/0173821 A1* | 7/2008 | Koltick | G01T 1/185 250/369 |
| 2013/0240748 A1* | 9/2013 | Friedman | G01T 1/185 250/375 |

FOREIGN PATENT DOCUMENTS

| | | |
|---|---|---|
| JP | 2008-232971 A | 10/2008 |
| JP | 2010-032451 A | 2/2010 |

OTHER PUBLICATIONS

International Search Report dated Nov. 29, 2016 for the PCT Application PCT/JP2016/078823.
Written Opinion dated Nov. 29, 2016 for the PCT Application PCT/JP2016/078823.

* cited by examiner

NUCLEAR MEDICINE EXAMINATION APPARATUS AND NUCLEAR MEDICINE EXAMINATION METHOD

CROSS-REFERENCE TO RELATED APPLICATIONS

This application is based upon and claims the benefit of priority from the prior Japanese Patent Application No. 2015-193543, filed on Sep. 30, 2015, and PCT International Patent Application No. PCT/JP2016/078823, filed on Sep. 29, 2016, the entire contents of which are incorporated herein by reference.

FIELD

The present invention relates to a nuclear medicine examination apparatus incorporating a Compton camera.

BACKGROUND

A radiation detection device (micro pixel gas chamber (MPGC)) using gas amplification by pixel-type electrodes has been studied. A radiation detection device using MPGC is combined with a scintillator to form an electron-tracking Compton camera (ETCC). A Compton camera of this type is featured to be able to implement imaging of a detection region that has insufficiently been imaged by radiation detection using a conventional detector (scintillator and semiconductor detector).

Japanese Patent No. 3354551 discloses an example of the structure of a radiation detection device using MPGC. Japanese Patent No. 3535045 also discloses an example of a Compton camera using a micros strip gas chamber (MSGC) instead of MPGC.

SUMMARY

A nuclear medicine examination apparatus according to an embodiment of the present invention is a nuclear medicine examination apparatus including a pixel-type radiation detection device configured to detect information of a charged particle generated by Compton scattering in a gas, one or a plurality of sensors configured to detect a physical amount of the gas in a chamber and a controller configured to control at least one of the physical amount and a composition of the gas based on output signals from the one or plurality of sensors.

According to an embodiment of the present invention, there is provided a nuclear medicine examination method of specifying a position of a radiation source emitted from a specimen by detecting a charged particle generated by Compton scattering in a gas. The method includes adjusting a pressure of a gas that causes the Compton scattering when detecting radiation emitted from the radiation source.

According to an embodiment of the present invention, there is provided a nuclear medicine examination method of specifying a position of a radiation source emitted from a specimen by detecting a charged particle generated by Compton scattering in a gas. The method includes adjusting a type of gas that causes the Compton scattering when detecting radiation emitted from the radiation source.

DESCRIPTION OF EMBODIMENTS

Figure 1:
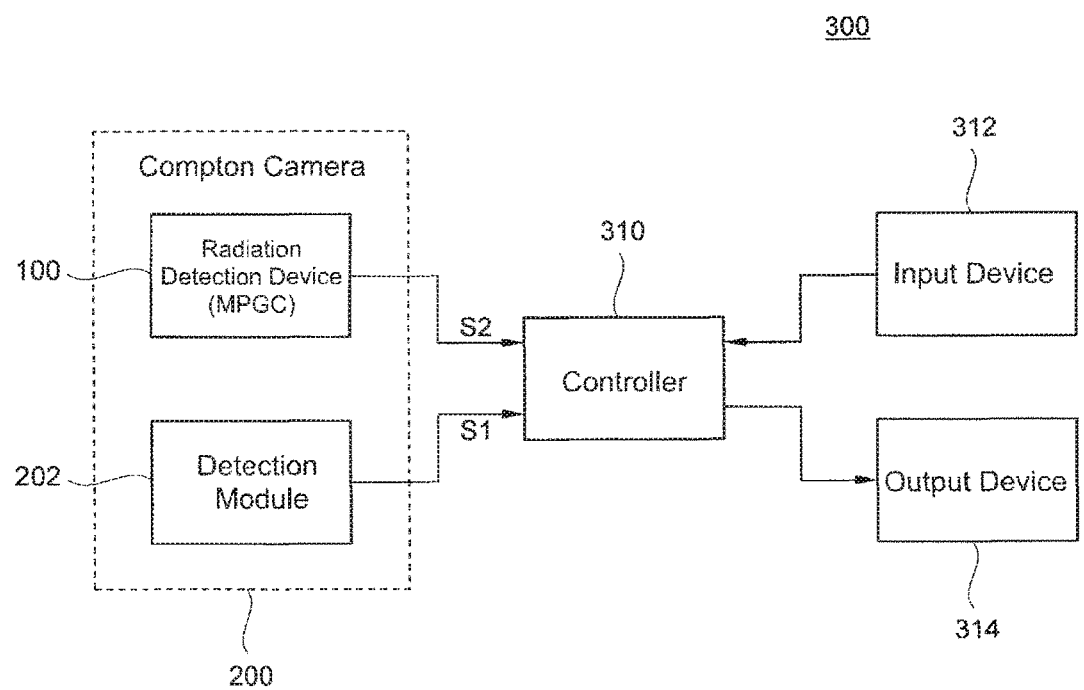
FIG. 1 is a block diagram showing the arrangement of a nuclear medicine examination apparatus.

A nuclear medicine examination apparatus according to the present invention will be described in detail below with reference to the accompanying drawings. Note that the nuclear medicine examination apparatus according to the present invention is not limited to the following embodiments and can be variously modified and embodied. In all the embodiments, the same reference numerals denote the same constituent elements. Furthermore, for the sake of descriptive convenience, dimensional ratios in the accompanying drawings are sometimes different from actual ratios, and an illustration of some components is sometimes omitted from the drawings.

The Compton camera is sometimes used as a nuclear medicine examination apparatus for executing a nuclear medicine examination called PET (Positron Emission Tomography) or SPECT (Single Photon Emission CT). In this case, a radiation source is a radioactive material embedded in the body of a patient. As a radioactive material to be administered into the human body, a material having a relatively short half-life is generally used to minimize the influence of radiation exposure. For this reason, in some cases, the intensity of radiation significantly decreases during an examination, resulting in failure to clearly specify the position of a radiation source.

To solve this problem, the sensitivity of a Compton camera may be increased to make it possible to clearly specify the position of a radiation source in spite of a reduction in the intensity of radiation. Specific methods for increasing the sensitivity include increasing the pressure of a gas, increasing the volume of a sensitive area by increasing the capacity of a chamber (increasing drift), and using a gas having a large reactive cross-section.

However, increasing the pressure of a gas or using a gas having a large reactive cross-section tends to cause abnormal discharge at a pixel-type electrode. In addition, increasing the capacity of a chamber or using a gas having a large reactive cross-section will prolong the drift time. This increases the probability that before the electron cloud generated by the scattering of the first incident ray finishes drifting, an electron cloud is generated by the scattering of the second incident ray and starts drifting. When two or more electron clouds are simultaneously generated in this manner, it is difficult to specify the position of the radiation source. In addition, even increasing the reactive cross-section will not prolong the drift time. This tends to cause abnormal discharge.

An embodiment of the present invention discloses a nuclear medicine examination apparatus that can specify the position of a radiation source with a predetermined efficiency over a long period of time.

FIG. 1 shows the configuration of a nuclear medicine examination apparatus 300 according to present embodiment. The nuclear medicine examination apparatus 300 includes a Compton camera 200, a controller 310, an input device 312, and an output device 314. In a medical site, the nuclear medicine examination apparatus 300 is used to specify the position of a radiation source embedded in the body of a patient. As will be described below, the Compton camera 200 has a chamber in which an introduced gas exists (in other words, a chamber into which a gas is introduced), and specifies the position of a radiation source by detecting the information of a charged particle generated by Compton scattering in the gas.

The controller 310 reconstructs a three-dimensional image by computation based on detection signals S1 and S2 output from the Compton camera 200, and specifies the position of a radiation source. The operator can instruct the controller 310 by using the input device 312. The three-dimensional image reconstructed by the controller 310 is presented to the operator via the output device 314.

The Compton camera 200 is an ETCC and includes the radiation detection device 100 using MPGC and a detection module 202. The detection module 202 in this case includes photomultiplier tubes each of which converts emitted light when a scattered γ ray enters the scintillator into an electrical signal. Installing a plurality of photomultiplier tubes makes it possible to specify a light emission position. Assume that the detection module 202 includes photomultiplier tubes in the following description.

Figure 2A:
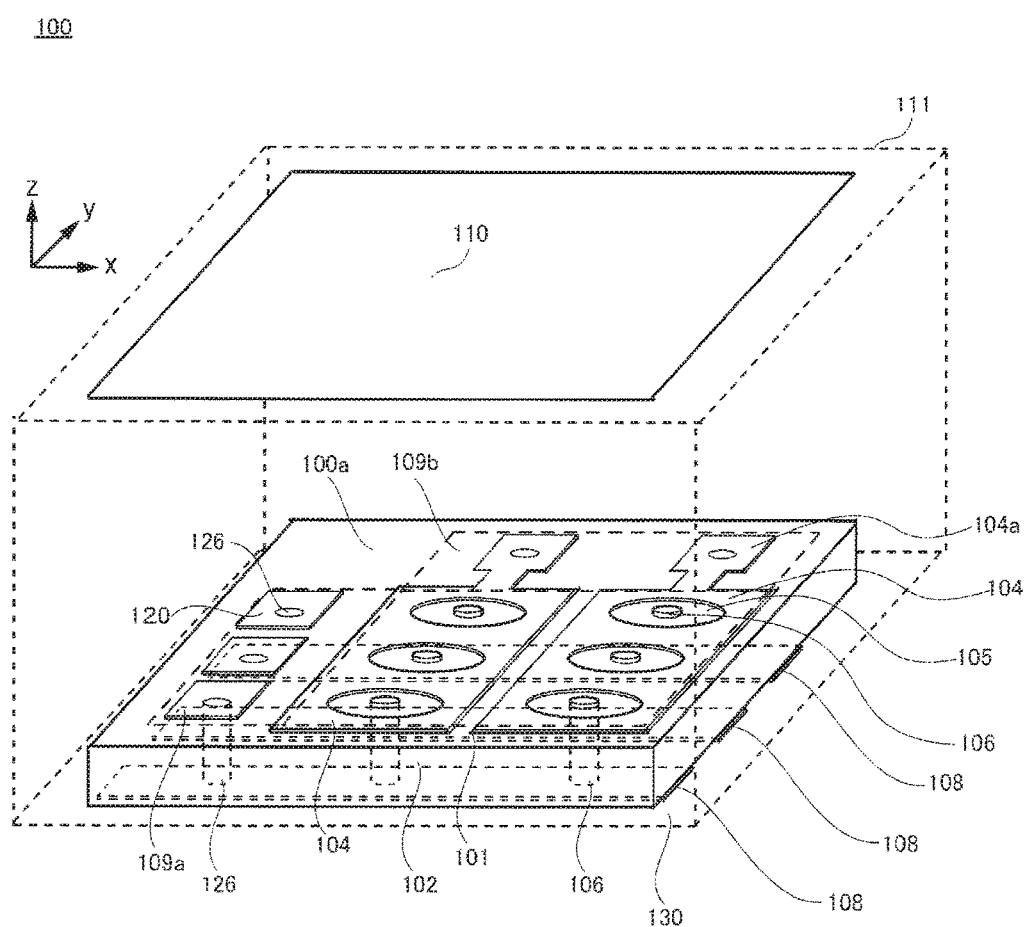
FIG. 2A is a view showing the schematic arrangement of a detection element of a radiation detection device.

FIG. 2A shows the schematic configuration of a detection element 100a of a radiation detection device 100. The radiation detection device 100 includes the detection element 100a having a pixel electrode portion 101 and connecting terminal portions 109 (109a and 109b) and a drift electrode 110. The detection element 100a and the drift electrode 110 are provided in a chamber 111. The detection element 100a is an element including the pixel electrode portion 101 and the connecting terminal portions 109 (109a and 109b).

The pixel electrode portion 101 of the radiation detection device 100 includes an insulating member 102, cathode electrodes 104, anode electrodes 106, anode electrode patterns 108, and a substrate 130. The plurality of cathode electrodes 104 are arranged on the first surface of the insulating member 102. The cathode electrodes 104 have a plurality of opening portions 105. The cathode electrode 104 is formed into a strip shape and hence is also called a cathode strip electrode.

The anode electrode 106 is placed in a through hole provided in the insulating member 102 from the second surface on the opposite side to the first surface of the insulating member 102. In this embodiment, the tip ends of the anode electrodes 106 are exposed in the plurality of opening portions 105 in the cathode electrode 104. Referring to FIG. 2A, each anode electrode 106 has a shape with its tip end being exposed in a corresponding one of the opening portions 105. However, each anode electrode 106 may be shaped such that its tip end is not exposed in a corresponding one of the opening portions 105 (including an anode electrode shaped such that its tip end is almost flush with the upper surface of the insulating member 102 (the upper surface of the through hole) or its tip end is located inside the through hole of the insulating member 102).

The plurality of anode electrodes 106 placed in the plurality of opening portions 105 of one cathode electrode 104 are respectively connected to the plurality of anode electrode patterns 108. The anode electrode pattern 108 extends to the connecting terminal portion 109a. The direction in which the cathode electrode 104 extends is almost vertical to the direction in which the anode electrode pattern 108 extends. This embodiment has exemplified the mode in which the anode electrodes 106 and the anode electrode patterns 108 are separately provided and are electrically connected to each other. However, this is not exhaustive, and the anode electrodes 106 and the anode electrode patterns 108 to which the respective anode electrodes 106 are connected may be integrally formed. Each anode electrode pattern 108 is formed into a strip shape and hence is also called an anode strip pattern.

The wiring terminal portion 109a includes a via hole 126 connected to the anode electrode pattern 108 and a metal layer 120. The metal layer 120 is connected to the via hole 126. Although FIG. 2A shows a case in which the anode electrode patterns 108 and the via holes 126 are separately formed, this is not exhaustive, and the anode electrode patterns 108 and the via holes 126 may be formed from the same metal material. The wiring terminal portion 109b includes an electrode 104a which is an extended portion of the cathode electrode 104.

With the above arrangement, the radiation detection device 100 has the anode electrodes 106 arranged in a matrix pattern on the pixel electrode portion 101. That is, the radiation detection device 100 has a plurality of "pixels" arranged, each including the anode electrode 106 and a portion of the cathode electrode 104. In this arrangement, a voltage is applied between each cathode electrode 104 and the corresponding anode electrode 106 to form an electric field.

The drift electrode 110 is placed to face the pixel electrode portion 101. The cathode electrodes 104 of the pixel electrode portion 101 are grounded, and a voltage is applied between the drift electrode 110 and each cathode electrode 104 to from an electric field.

The chamber 111 encloses the pixel electrode portion 101, the connecting terminal portions 109, and the drift electrode 110. A gas mixture of a rare gas such as argon or xenon and a molecular gas such as ethane or methane is introduced into the chamber 111.

Figure 2B:
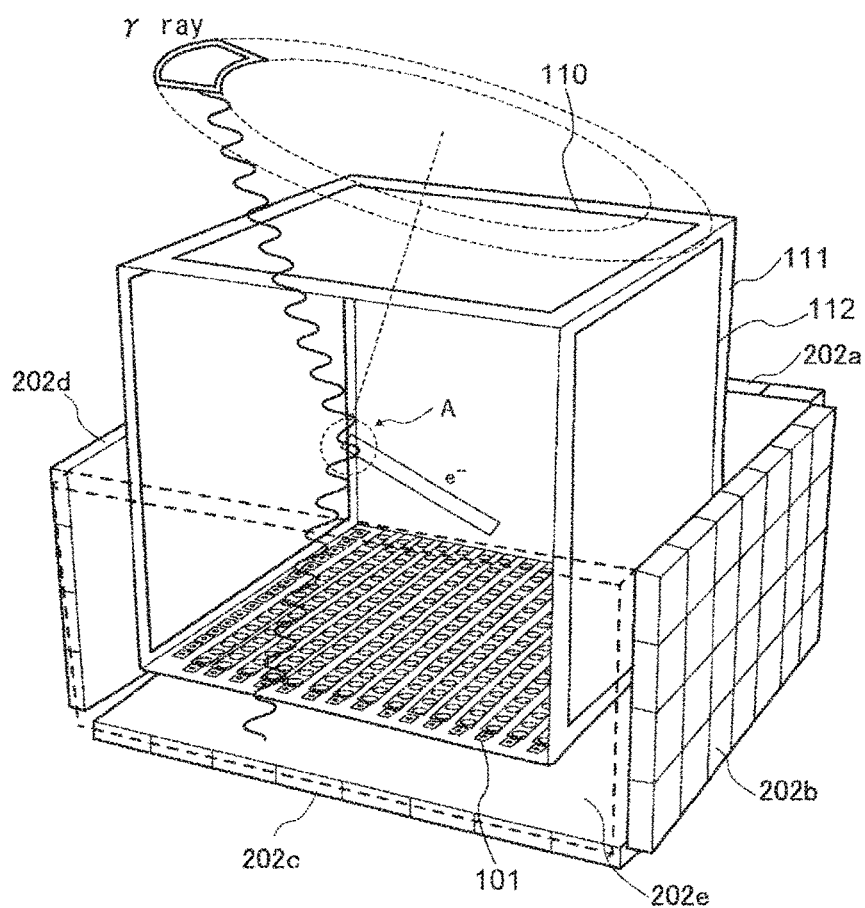
FIG. 2B is a view showing the schematic arrangement of a Compton camera.

FIG. 2B shows the schematic arrangement of the detection module 202. As shown in FIG. 2B, the detection module 202 is provided to surround the radiation detection device 100 from five directions. In an example shown in FIG. 2B, the detection module has five portions 202a to 202e. Note that the detection module need not always be installed to surround the radiation detection device from five directions and may be installed in conformity with a specimen (radiation source) in the examination apparatus, as needed. For example, a detection module may be provided in only one direction.

As shown in FIG. 2B, the radiation detection device 100 has the chamber 111. A gas mixture of a rare gas such as argon or xenon and an alkane gas (a chain saturate hydrocarbon represented by the general formula $C_nH_{2n+2}$) at room temperature such as ethane or methane or a gas having a quenching effect (quenching gas) including carbon dioxide is introduced into the chamber 111. A gas or gases to be mixed with a rare gas may include either or both of a gas such as ethane or methane and a gas having a quenching effect including carbon dioxide. The pixel electrode portion 101 on which a plurality of pixels is two-dimensionally laid out is provided on the bottom surface of the chamber 111. The drift electrode 110 is provided on the upper surface of the chamber 111. Drift cages 112 are provided on side surfaces of the chamber 111. The drift cages 112 are provided to homogenize the electric field distribution between the drift electrode 110 and the pixel electrode portion 101.

The following description concerns the principle of the Compton camera 200. First of all, when a γ ray externally enters the radiation detection device 100, the incident γ ray collides with a gas in the chamber 111 and is scattered at a certain probability. Reference symbol "A" in FIG. 2B denotes a collision position. The scattered γ ray whose propagation direction is changed by the collision is transmitted through the radiation detection device 100 and enters the detection module 202. When the scattered γ ray enters the detection module 202, light emission occurs. A photomultiplier tube then converts this emitted light into an electrical signal. The electrical signal obtained in this manner corresponds to the detection signal S1 shown in FIG. 1. Information representing the energy of the scattered γ ray and the incident position and incident time of the scattered γ ray is provided to the controller 310. With this operation, an image is reconstructed within the limited energy range conceivable when radiation from a radiation source is scattered only once in the chamber 111, and hence the noise removing ability (noise removal by energy discrimination) can be improved.

On the other hand, the gas in the chamber 111 which has collided with the incident γ ray emits a recoil electron e$^-$ (charged particle) from the position denoted by reference symbol "A" in a predetermined direction. An electron cloud is then generated along the track of the recoil electron. The electrons constituting the electron cloud are attracted to the pixel electrode portion 101 due to an electric field between the drift electrode 110 and the pixel electrode portion 101. An electron that has been attracted near to the electrode portion 101 collides with the gas due to a high electric field near the pixel electrode portion 101 to ionize the gas. Ionized electrons proliferate in an avalanche-like manner and are detected by the pixel electrode portion 101. The electrical signal obtained in this manner corresponds to the detection signal S2 shown in FIG. 1, and information representing the capturing position and capturing time of each electron is provided to the controller 310. The detection signal S2 is a signal that makes it possible to specify the position of a pixel that has detected the electron and the time when the pixel has detected the electron.

Note that the time between the instant when a scattered γ ray enters the detection module 202 and the instant when an electron is detected by the pixel electrode portion 101 makes it possible to calculate the distance from the pixel electrode portion 101 to the position at which an electron cloud is generated (the position in the z direction).

Figure 2C:
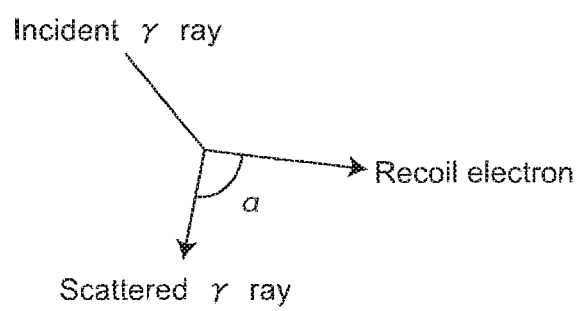
FIG. 2C is a view for explaining the relationship between an incident γ ray, a scattered γ ray, and a recoil electron.

The controller 310 is triggered by the activation of the detection signal S1 (the incidence of a scattered γ ray on the detection module 202) to chronologically analyze the detection signal S2 and calculate the track of a recoil electron by using the position of a pixel that has detected an electron and the time when the pixel has detected the electron (to be sometimes referred to as a detection time hereinafter). The detection time (to be sometimes referred to as a drift time hereinafter) corresponds to the time from the instant when the controller 310 is triggered to the instant when an electron is detected by the pixel electrode portion 101. Calculating also an angle a shown in FIG. 2C can specify the direction in which the incident γ ray has entered. The controller 310 acquires three-dimensional coordinates indicating the position of a radiation source from the direction specified in this manner. The controller 310 also acquires a count rate representing the intensity of the radiation source from the detection signals S1 and S2. Four-dimensional data constituted by the three-dimensional coordinates acquired in this manner and the count rate is an indicated value from the Compton camera 200.

Figure 3:
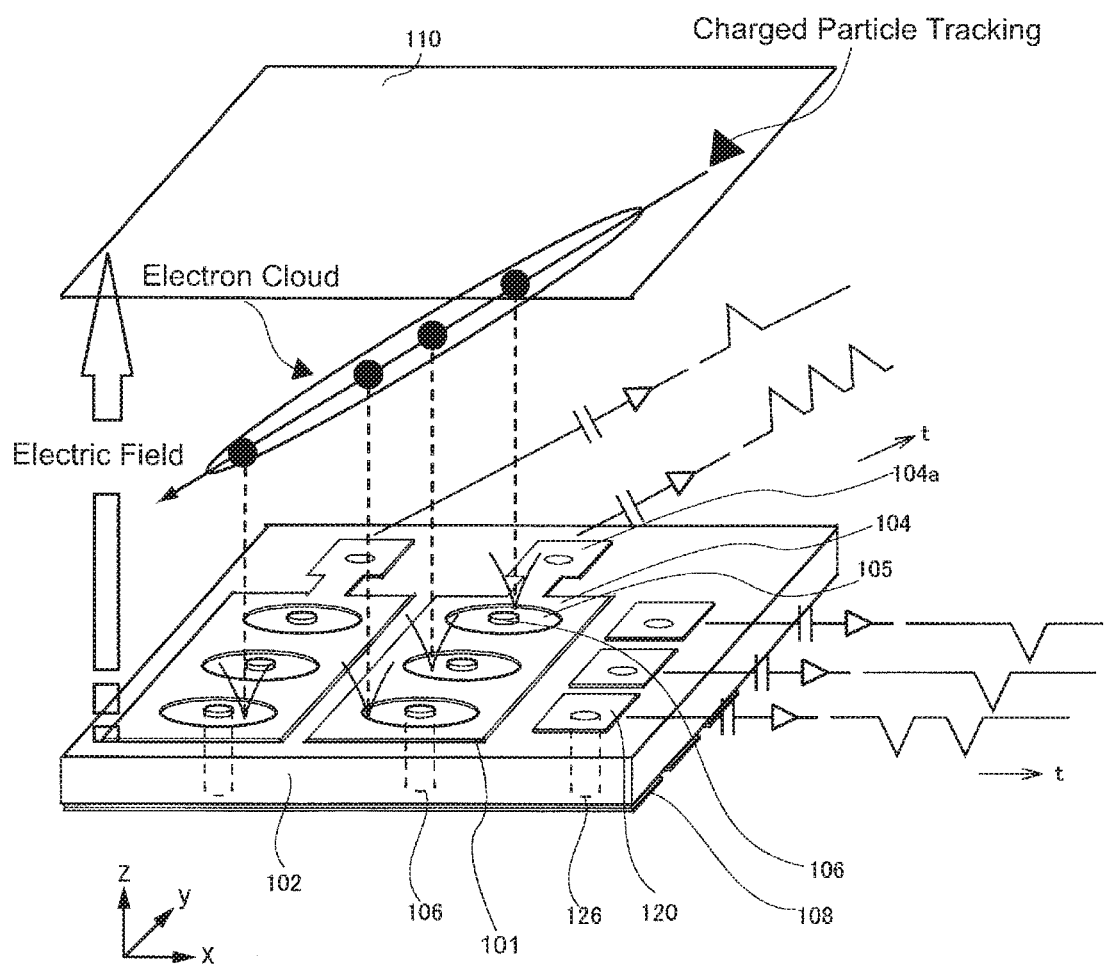
FIG. 3 is a view showing the schematic arrangement of a radiation detection device.

As shown in FIG. 3, the pixel electrode portion 101 includes the insulating member 102, the cathode electrodes 104, the anode electrodes 106, and the anode electrode patterns 108.

The plurality of cathode electrodes 104 extend in the y direction on the upper surface of the insulating member 102. The cathode electrode 104 is provided with the plurality of opening portions 105. The upper surface of the insulating member 102 is exposed in the opening portions 105.

The anode electrodes 106 extend from the reverse surface of the insulating member 102 and penetrate through the insulating member 102 in the z direction. The tip ends of the anode electrodes 106 are exposed in the plurality of opening portions 105.

The plurality of anode electrodes 106 arrayed in the y direction are respectively connected to the different anode electrode patterns 108. The plurality of anode electrode patterns 108 extend in the x direction on the reverse surface of the insulating member 102. The y direction in which the cathode electrodes 104 extend is almost perpendicular to the x direction in which the anode electrode patterns 108 extend. This embodiment has exemplified the mode in which the anode electrodes 106 and the anode electrode patterns 108 are separately provided and are electrically connected to each other. However, this is not exhaustive, and the anode electrodes 106 and the anode electrode patterns 108 may be integrally formed.

A voltage is applied between the cathode electrode 104 and the anode electrode 106 to form an electric field. The anode electrode 106 captures an electron attracted to the pixel electrode portion 101 due to this electric field. This pixel then detects the electron.

The drift electrode 110 has an xy plane is separated from the xy plane forming the pixel electrode portion 101 by a predetermined distance in the z direction. A voltage is applied between the drift electrode 110 and the cathode electrode 104 and the anode electrode 106 to form an electric field.

The radiation detection device 100 according to this embodiment has the above arrangement, in which the anode electrodes 106 are arranged in a matrix pattern in the pixel electrode portion 101. The anode electrode 106 exposed on the upper surface of the insulating member 102 forms one pixel. Chronologically analyzing changes in the voltages of electrical signals appearing in the plurality of cathode electrodes 104 and the plurality of anode electrode patterns 108 can specify the positions of pixels that have detected electrons and the detection times of the electrons, thus obtaining electron detection results at the respective pixels. As has been described above, this makes it possible to calculate the track of a recoil electron.

FIRST EMBODIMENT

Figure 4:
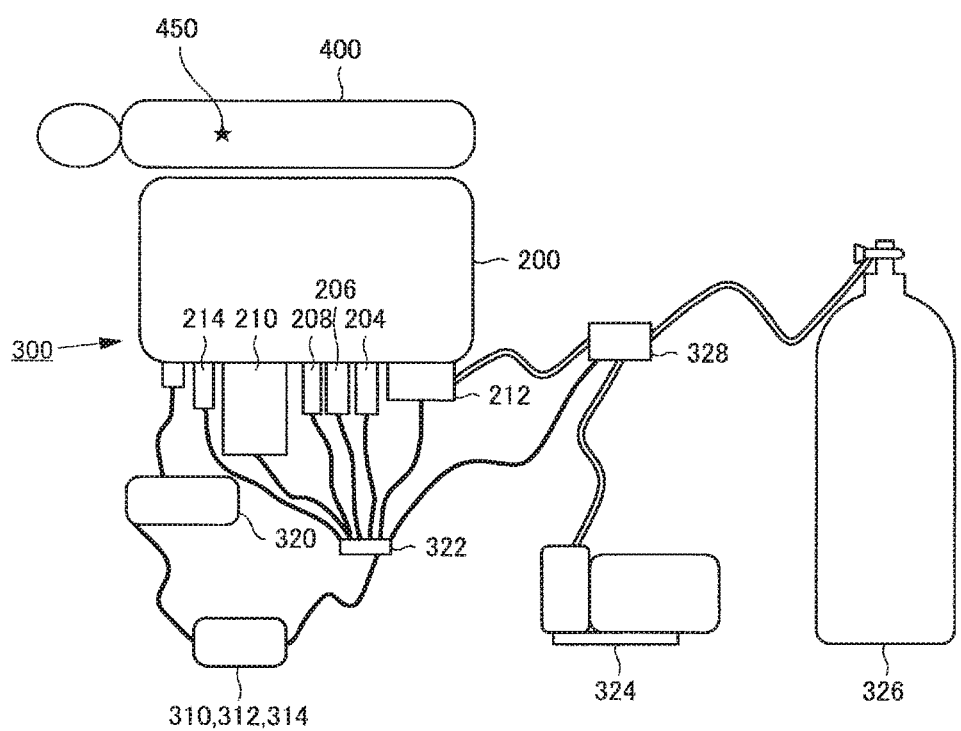
FIG. 4 is a schematic view showing a nuclear medicine examination apparatus and its peripheral devices according to Example 1.

FIG. 4 is a schematic view showing a nuclear medicine examination apparatus 300 and its peripheral devices shown in FIG. 1. As shown in FIG. 4, the nuclear medicine examination apparatus 300 is used to specify the position of a radiation source 450 embedded in a human body 400.

As shown in FIG. 4, a controller 310, an input device 312, and an output device 314, which are shown in FIG. 1, are implemented by a computer. The controller 310 is formed from a CPU provided in this computer. The input device 312 is formed from an input device such as a keyboard, mouse, or the like provided for this computer. The output device 314 is formed from a display device such as a display provided for the computer.

The nuclear medicine examination apparatus 300 is provided with various types of sensors including a pressure sensor 204, a temperature sensor 206, and a mass analyzer 208, a radiation sensor signal detector 210, an electromagnetic valve 212, and a temperature control mechanism 214. They are connected to the controller 310 via a hub 322.

The pressure sensor 204 is a sensor that measures the pressure in a chamber 111 of a radiation detection device 100 shown in FIG. 2A and FIG. 2B. An output signal from the pressure sensor 204 is supplied to the controller 310 via the hub 322. As a specific example of the pressure sensor 204, for example, an absolute pressure instrument that can measure an absolute pressure such as a diaphragm vacuum meter is preferably used. Note, however, that even a differential pressure instrument that cannot measure an absolute pressure by itself can be used as the pressure sensor 204 when an absolute pressure instrument is provided to use indicated values from the differential pressure instrument and the absolute pressure instrument in synchronism with each other.

The temperature sensor 206 is a sensor that measures the temperature in the chamber 111. An output signal from the temperature sensor 206 is supplied to the controller 310 via the hub 322. The temperature sensor 206 may be provided in the chamber 111 or on the outer surface of the chamber 111. As a specific example of the temperature sensor 206, a K- or T-type thermocouple is preferably used.

The mass analyzer 208 is a sensor that measures the composition ratio of each gas in the chamber 111. The mass analyzer 208 samples the gas in the chamber 111 and a gas mixture of a rare gas in the chamber 111 and a gas having a quenching effect (quenching gas), thus performing mass analysis. An output signal from then mass analyzer 208 is supplied to the controller 310 via the hub 322.

The radiation sensor signal detector 210 has a function of generating the detection signals S1 and S2 described above. The detection signals S1 and S2 generated by the radiation sensor signal detector 210 are supplied to the controller 310 via the hub 322.

The electromagnetic valve 212 is connected to a gas cylinder 326 and a vacuum pump 324 via an electromagnetic regulator branch valve 328. The gas cylinder 326 is filled with a rare gas and a gas having a quenching effect (quenching gas). For example, the gas cylinder 326 is filled with a gas mixture containing argon and ethane at a ratio of 9:1. The electromagnetic regulator branch valve 328 is connected to the controller 310 via the hub 322, and the electromagnetic valve 212 and the electromagnetic regulator branch valve 328 are configured to open and close under the control of the controller 310.

The temperature control mechanism 214 has a function of controlling the temperature in the chamber 111 under the control of the controller 310. More specifically, the temperature control mechanism 214 may be either or both of a heating mechanism and a cooling mechanism. As the heating mechanism, for example, a heating wire is preferably used. On the other hand, as the cooling mechanism, for example, an air-cooling mechanism using a fan or a water-cooling mechanism obtained by passing water through a tube is preferably used. The specific installation place of the temperature control mechanism 214 may be inside or outside the chamber 111.

The nuclear medicine examination apparatus 300 is further provided with a high-voltage power supply 320. The high-voltage power supply 320 has a function of generating high-voltage power under the control of the controller 310 and supplying the power as operating power to the Compton camera 200.

Figure 5:
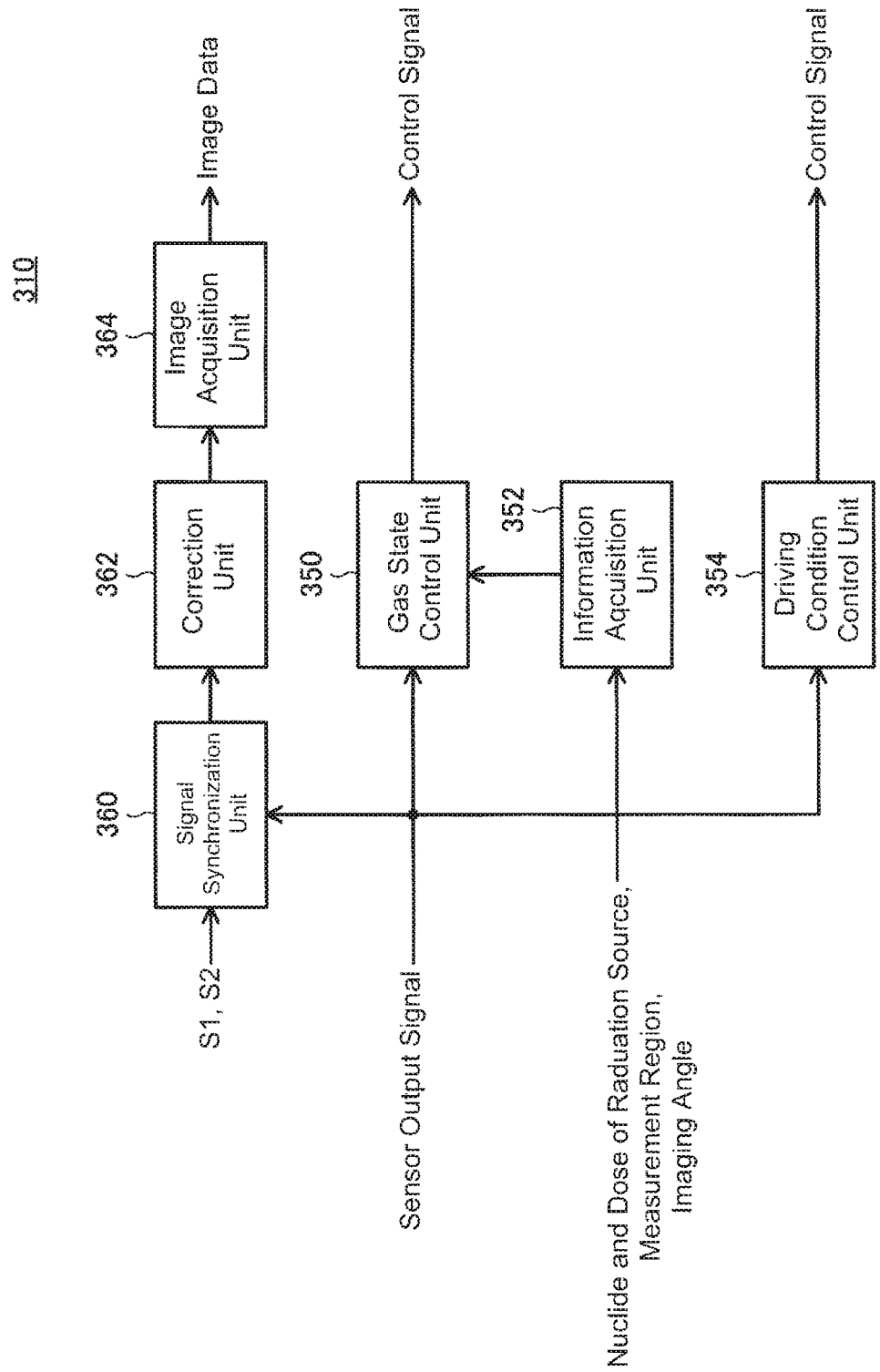
FIG. 5 is a schematic block diagram showing the function blocks of a controller.

FIG. 5 is a schematic block diagram showing the function blocks of the controller 310. As shown in FIG. 5, the controller 310 functionally includes a gas state control unit 350, an information acquisition unit 352, a driving condition control unit 354, a signal synchronization unit 360, a correction unit 362, and an image acquisition unit 364.

The gas state control unit 350 is a functional unit that controls a gas state in the chamber 111 shown in FIG. 2A and FIG. 2B (controls at least one of physical amounts such as a temperature and a pressure and a composition) on the basis of output signals from various types of sensors shown in FIG. 4 (the pressure sensor 204, the temperature sensor 206, and the mass analyzer 208). More specifically, gas state control by the gas state control unit 350 includes controlling the pressure in the chamber 111 on the basis of an output signal from the pressure sensor 204, controlling the temperature in the chamber 111 on the basis of an output signal from the temperature sensor 206, and controlling the composition ratio of the gas in the chamber 111 on the basis of an output signal from the mass analyzer 208. Each control operation will be described in detail below.

Figure 6:
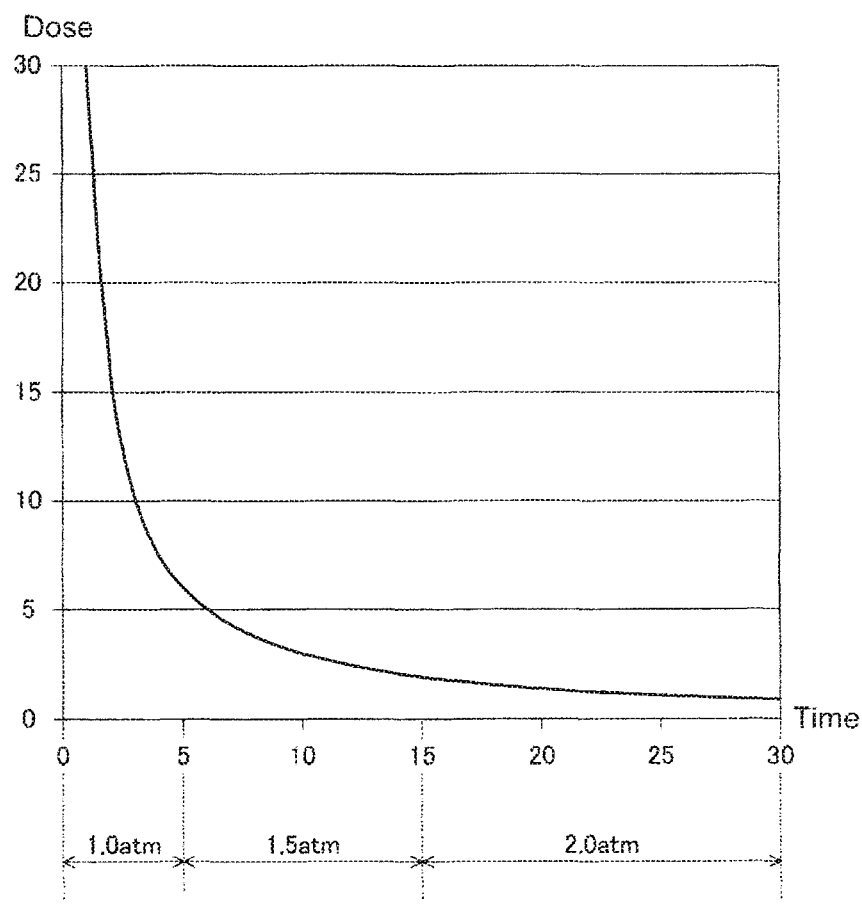
FIG. 6 is a graph showing a temporal change in the dose of radiation from a radiation source and desired values of pressure control by a gas state control unit.

First of all, with regard to pressure, FIG. 6 shows a temporal change in the dose of radiation from the radiation source 450, and desired values of pressure control by the gas state control unit. 350. As shown in FIG. 6, the dose of radiation from the radiation source 450 exhibits the property of decreasing in inverse proportion to the lapse of time. As the dose of radiation from the radiation source 450 decreases, the probability of Compton scattering decreases. This makes it difficult for the image acquisition unit 364 to reconstruct a three-dimensional image and specify the position of the radiation source 450. For this reason, the gas state control unit 350 raises the pressure in the chamber 111 with the lapse of time. More specifically, the gas state control unit 350 monitors the pressure in the chamber 111 in accordance with an output signal from the pressure sensor 204, and controls the electromagnetic valve 212 and the electromagnetic regulator branch valve 328, thereby raising the pressure in the chamber 111. In the case shown in FIG. 6, the pressure in the chamber 111 is set to 1.0 atm for first 5 min, and the pressure in the chamber 111 is set to 1.5 atm for next 10 min. Subsequently, the pressure in the chamber 111 is set to 2.0 atm.

Raising the pressure of a gas in the chamber 111 makes it possible to properly specify the position of the radiation source 450 even if the dose of radiation from the radiation source 450 is low. On the other hand, as described above, raising the pressure of a gas while the dose of radiation is high tends to cause abnormal discharge at the pixel electrode portion 101. The gas state control unit 350 gradually raises the pressure in the chamber 111 with the lapse of time as described above, and hence can specify the position of the radiation source 450 with a predetermined efficiency over a long period of time while preventing the occurrence of such abnormal discharge.

Subsequently, with regard to temperature, the gas state control unit 350 operates to keep the temperature in the chamber 111 constant by controlling the temperature control mechanism 214 while monitoring the temperature in the chamber 111 in accordance with an output signal from the temperature sensor 206. This can keep the temperature in the chamber 111 constant and hence can specify the position of the radiation source 450 with a predetermined efficiency over a long period of time.

Subsequently, with regard to the composition ratio of the gas, the gas state control unit 350 operates to keep the composition ratio of the gas in the chamber 111 constant by controlling the electromagnetic valve 212 and the electromagnetic regulator branch valve 328 while monitoring the composition ratio of the gas in the chamber 111 in accordance with an output signal from the mass analyzer 208. The gas in the chamber 111 deteriorates with the lapse of time, and the composition ratio of the gas changes. However, performing such control can keep the composition ratio of the gas in the chamber 111 constant, and hence can specify the position of the radiation source 450 with a predetermined efficiency over a long period of time.

The information acquisition unit 352 is a functional unit that acquires information concerning at least one of the following information: the nuclide and dose data of the radiation source 450, a measurement region in the human body 400, and an imaging angle (the angle of the Compton camera 200 with respect to the human body 400). Of these pieces of information, the nuclide of the radiation source 450, a measurement region in the human body 400, and an imaging angle may be set in the controller 310 by the user. The dose data of the radiation source 450 may be sequentially acquired from the above count rate or may be sequentially acquired from output data from a dosimeter that is provided separately from the Compton camera 200.

The information acquired by the information acquisition unit 352 is supplied to the gas state control unit 350. The gas state control unit 350 stores the contents of the information supplied from the information acquisition unit 352 in association with the specific contents of each control operation described above, and acquires the specific contents of the respective control operations on the basis of the information supplied to the gas state control unit 350. The gas state control unit 350 then executes each control operation in accordance with the acquired contents. That is, because the specific contents of control performed by the gas state control unit 350 are automatically adjusted on the basis of the information acquired by the information acquisition unit 352, the position of the radiation source 450 can be specified with constant quality regardless of the skill of an imaging technician.

The driving condition control unit 354 is a functional unit that controls driving conditions for the Compton camera 200 shown in FIG. 4 on the basis of output signals from the respective types of sensors shown in FIG. 4 (the pressure sensor 204, the temperature sensor 206, and the mass analyzer 208). The driving conditions in this case include the potential of the anode electrode 106 and the potential of the drift electrode 110 shown in, for example, FIG. 3.

In some cases, if, for example, the pressure in the chamber 111 is high, discharge occurs, and the gain of avalanche amplification becomes excessively high. If the pressure in the chamber 111 is high, the driving condition control unit 354 lowers the potential of the anode electrode 106 to restrict the occurrence of discharge and also restrict an increase in the gain of avalanche amplification. In addition, the driving condition control unit 354 can adjust a region for making a recoil electron drift by controlling the potential of the drift electrode 110 on the basis of output signals from various types of sensors. The driving condition control unit 354 can control the Compton camera 200 in a desired state by controlling driving conditions for the Compton camera 200 on the basis of output signals from various types of sensors in this manner. This control, therefore, makes it possible to specify the position of the radiation source 450 with constant quality.

The signal synchronization unit 360 is a functional unit that associates output signals from the respective types of sensors shown in FIG. 4 (the pressure sensor 204, the temperature sensor 206, and the mass analyzer 208) with the detection signals S1 and S2 from the Compton camera 200 described above. With the processing performed by the signal synchronization unit 360, output signals from various types of sensors at different times are associated with the detection signals S1 and S2 sequentially supplied from the Compton camera 200 in a chronological order.

The correction unit 362 is a functional unit that corrects the detection signals S1 and S2 sequentially supplied from the Compton camera 200 in a chronological order on the basis of output signals from the respective types of sensors associated with the detection signals S1 and S2. Although the detection signals S1 and S2 from the Compton camera 200 are influenced by the pressure, temperature, and gas composition ratio in the chamber 111, the correction unit 362 can remove such influences from the detection signals S1 and S2 by performing the above correction.

The image acquisition unit 364 is a functional unit that acquires an image on the basis of the detection signals S1 and S2 corrected by the correction unit 362. More specifically, a three-dimensional image is reconstructed by computation based on the detection signals S1 and S2. The image obtained in this manner is presented to the operator via the output device 314 shown in FIG. 1, as described above.

As described above, the nuclear medicine examination apparatus 300 according to this embodiment can specify the position of the radiation source 450 with a constant efficiency over a long period of time because the gas state control unit 350 controls a gas state in the chamber 111 on the basis of output signals from the respective types of sensors (the pressure sensor 204, the temperature sensor 206, and the mass analyzer 208). In addition, because the specific contents of control performed by the gas state control unit 350 are automatically determined on the basis of the information acquired by the information acquisition unit 352, the position of the radiation source 450 can be specified with constant quality regardless of the skill of an imaging technician. In addition, it is possible to specify the position of the radiation source 450 with constant quality by making the driving condition control unit 354 control driving conditions for the Compton camera 200 on the basis of output signals from the respective types of sensors. In addition, the correction unit 362 can eliminate the influences of the pressure, temperature, and gas composition ratio in the chamber 111 from the detection signals S1 and S2 by making the correction unit 362 correct the detection signals S1 and S2.

Control of a gas state by the gas state control unit 350 and correction of the detection signals S1 and S2 by the correction unit 362 will be described in detail again with reference to a processing procedure for the controller 310.

Figure 7:
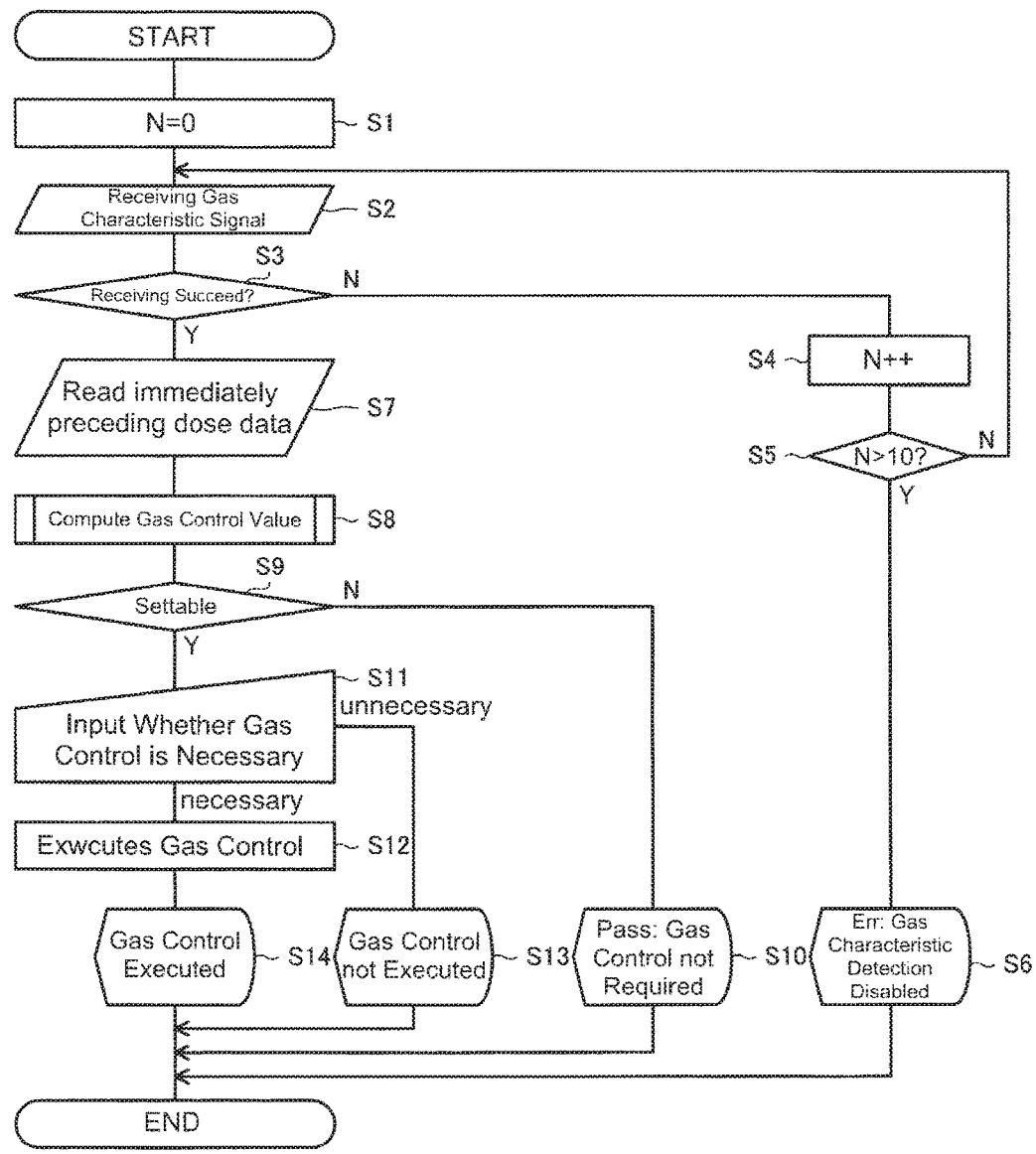
FIG. 7 is a flowchart showing a processing procedure for control of the physical amount of gas by the gas state control unit.

FIG. 7 is a flowchart showing a processing procedure for control of a gas state by the gas state control unit 350. Note that this processing procedure exemplifies a case in which the dose data of the radiation source 450 is used as information acquired by the information acquisition unit 352. As shown in FIG. 7, first of all, the gas state control unit 350 sets a variable N to 0 (step S1). The gas state control unit 350 then performs a receiving operation with respect to output signals (to be referred to as "gas characteristic signals" hereinafter) from the respective types of sensors (step S2). The gas state control unit 350 then determines whether the receiving operation has succeeded (step S3).

Upon determining in step S3 that the receiving operation has failed, the gas state control unit 350 increments the variable N by 1 (step S4), and determines whether the variable N has exceeded 10 (step S5). If NO in step S5, the gas state control unit 350 executes a receiving operation for a gas characteristic signal upon returning to step S2. If YES in step S5, the gas state control unit 350 displays "Err: gas characteristic detection disabled" on the output device 314 shown in FIG. 1 (step S6). The processing is terminated. In this case, gas control is not executed.

Upon determining in step S3 that the receiving operation has succeeded, the gas state control unit 350 reads immediately preceding dose data from the information acquisition unit 352 (step S7), and computes a desired value of control (to be referred to as a "gas control value" hereinafter) by using the read dose data and the gas characteristic signal received in step S2 (step S8). The information acquisition unit 352 determines whether the gas control value is included in a settable range (step S9). Upon determining that the gas control value is not included in the range, the information acquisition unit 352 displays "Pass: gas control not required" on the output device 314 shown in FIG. 1 (step S10), and terminates the processing. In this case as well, the gas state control unit 350 does not execute gas control.

Upon determining in step S9 that the gas control value is included, the gas state control unit 350 makes the user input information indicating whether gas control is necessary (step S11). This processing is preferably configured to make the user input information indicating whether control is necessary via the input device 312 upon presenting the settable range of gas control values to the output device 314 shown in FIG. 1.

If the user inputs information indicating that gas control is not unnecessary in step S11, the gas state control unit 350 displays "gas control not executed" on the output device 314 shown in FIG. 1 (step S13), and terminates the processing. In this case as well, the gas state control unit 350 does not execute gas control.

In contrast to this, if the user inputs information indicating that gas control is necessary in step S11, the gas state control unit 350 executes gas control so as to implement gas control values computed in step S8 (step S12). The gas state control unit 350 then displays "gas control executed" on the output device 314 shown in FIG. 1 (step S14), and terminates the processing.

As described above, the gas state control unit 350 can execute gas control by performing processing based on the processing procedure in FIG. 7.

Figure 8:
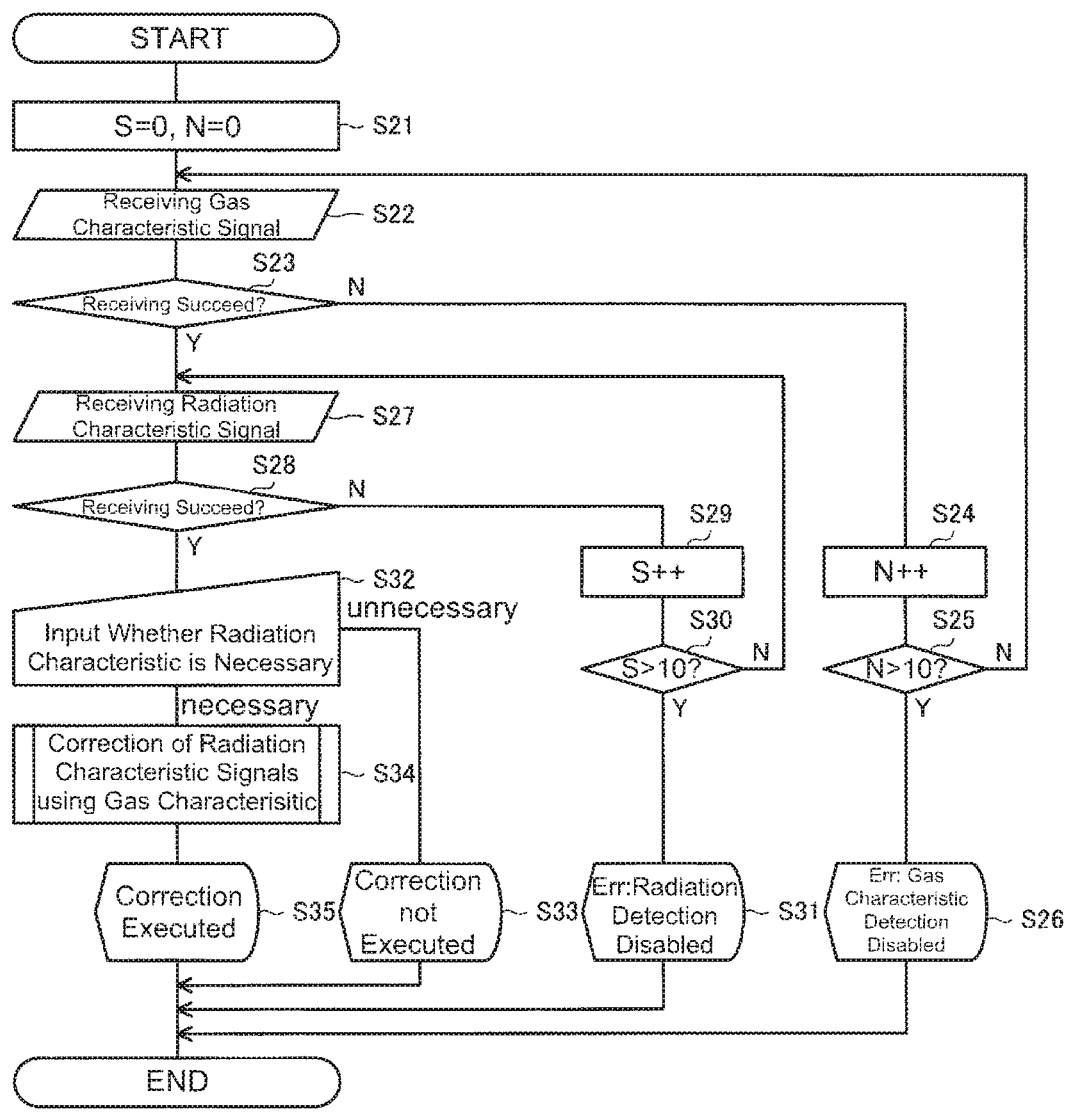
FIG. 8 is a flowchart showing a processing procedure for correction of detection signals S1 and S2 by a correction unit.

FIG. 8 is a flowchart showing a processing procedure for correction of the detection signals S1 and S2 (to be referred to as "radiation characteristic signals" hereinafter) by the correction unit 362. As shown in FIG. 8, the correction unit 362 sets variables S and N to 0 (step S21). The correction unit 362 then performs a receiving operation for a gas characteristic signal (step S22), and then determines whether the receiving operation has succeeded (step S23).

Upon determining in step S23 that the receiving operation has failed, the correction unit 362 increments the variable N by 1 (step S24), and determines whether the variable N has exceeded 10 (step S25). If NO in step S25, the correction unit 362 returns to step S22 to execute a receiving operation for a gas characteristic signal again. If YES in step S25, the correction unit 362 displays "Err: gas characteristic detection disabled" on the output device 314 shown in FIG. 1 (step S26), and terminates the processing. In this case, the correction unit 362 executes no radiation characteristic signal correction.

Upon determining in step S23 that the receiving operation has succeeded, the correction unit 362 performs a receiving operation for radiation characteristic signals (step S27), and determines whether the receiving operation has succeeded (step S28).

Upon determining in step S28 that the receiving operation has failed, the correction unit 362 increments the variable S by 1 (step S29), and determines whether the variable S has exceeded 10 (step S30). If NO in step S30, the correction unit 362 returns to step S27 to execute a receiving operation for radiation characteristic signals again. If YES in step S30, the correction unit 362 displays "Err: radiation detection disabled" on the output device 314 shown in FIG. 1 (step S31), and terminates the processing. In this case as well, the correction unit 362 executes no radiation characteristic signal correction.

Upon determining in step S28 that the receiving operation has succeeded, the correction unit 362 makes the user input information indicating whether radiation characteristic signal correction is necessary (step S32). This processing is preferably configured to make the user input information indicating whether correction is necessary via the input device 312.

If the user inputs information indicating that correction is not necessary in step S32, the correction unit 362 displays "correction not executed" on the output device 314 shown in FIG. 1 (step S33), and terminates the processing. In this case as well, the correction unit 362 executes no radiation characteristic signal correction.

If the user inputs information indicating that correction is necessary in step S32, the correction unit 362 executes correction of the radiation characteristic signals received in step S27 on the basis of the gas characteristic signal received in step S22 (step S34). The correction unit 362 then displays "correction executed" on the output device 314 shown in FIG. 1 (step S35), and terminates the processing.

In this manner, the correction unit 362 can execute correction of radiation characteristic signals by processing based on the processing procedure shown in FIG. 8.

Note that output signals from the respective types of sensors (the pressure sensor 204, the temperature sensor 206, and the mass analyzer 208) shown in FIG. 4 may be output to the output device 314 shown in FIG. 1 to allow the operator to visually check the measurement values of these sensors. This allows the operator to manually control a gas in the chamber 111.

This embodiment regards all the pressure, temperature, and gas composition ratio in the chamber 111 as control targets of the gas state control unit 350, but only some of them may be control targets. In addition, in the embodiment, the gas state control unit 350 performs gas control, the driving condition control unit 354 performs driving condition control, and the correction unit 362 performs correction of the detection signals S1 and S2. However, the embodiment may be configured to execute only some of these control operations.

FIG. 6 shows an example of intermittently (stepwisely) controlling the pressure in the chamber 111. However, the gas state control unit 350 may continuously control the pressure in the chamber 111. This applies to temperature and gas composition ratio.

Note that in an embodiment of the present invention, the chamber 111 of the radiation detection device 100 may be detachable. In addition, the detection element 100a may be configured to be detachable from the chamber 111. If, for example, the anode electrode 106 has deteriorated, the detection element 100a may be configured to be detachable and replaceable.

SECOND EMBODIMENT

Figure 9:
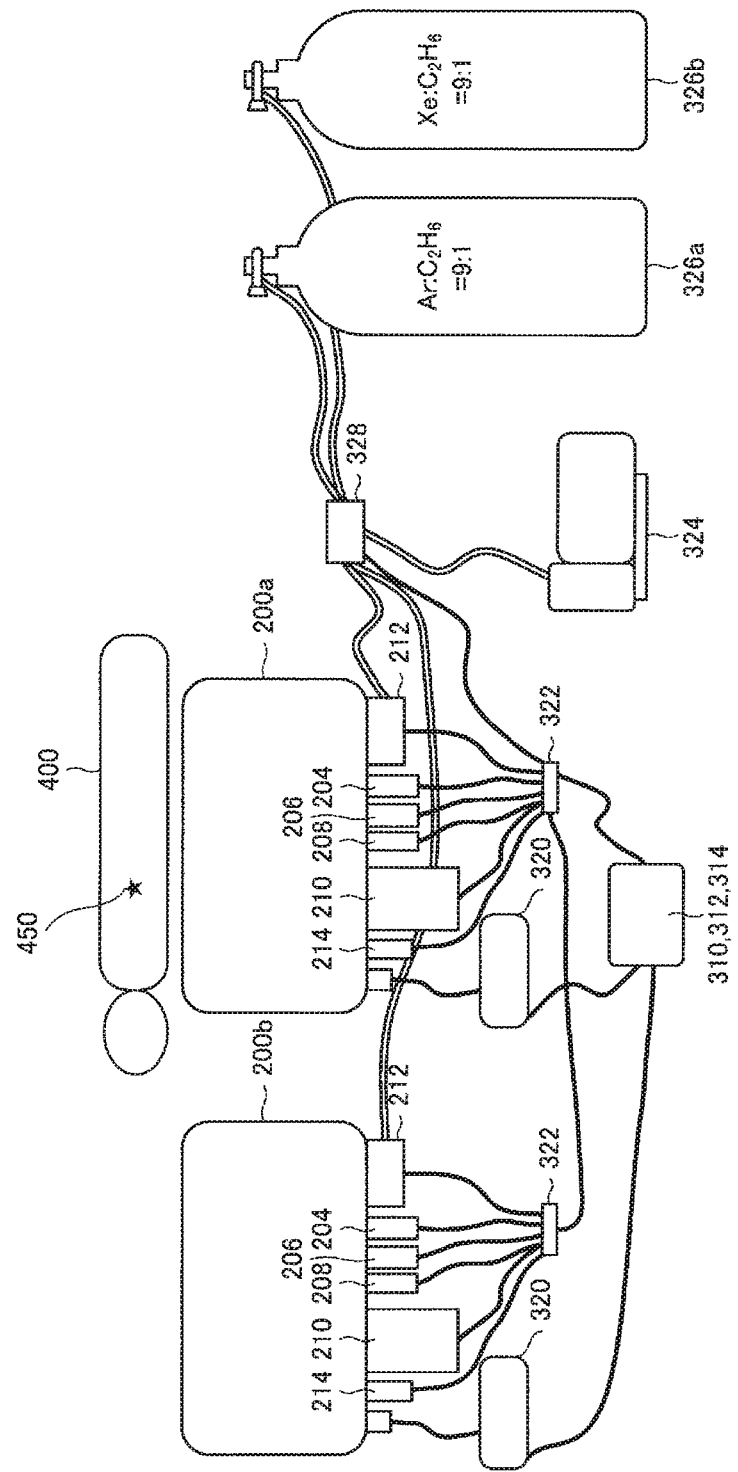
FIG. 9 is a schematic view showing a nuclear medicine examination apparatus and its peripheral devices according to second embodiment.

FIG. 9 is a schematic view showing a nuclear medicine examination apparatus 300 (see FIG. 1) and its peripheral devices according to the second embodiment. The nuclear medicine examination apparatus 300 includes a plurality of Compton cameras 200 and a plurality of gas cylinders 326. Each gas cylinder 326 is filled with a gas mixture containing a rare gas and a gas having a quenching effect (quenching gas) at a predetermined ratio. FIG. 9 shows, for example, two Compton cameras 200a and 200b and two gas cylinders 326a and 326b. However, the numbers of them are not limited to two.

The peripheral devices of the Compton camera 200 are basically provided for each Compton camera 200. More specifically, various types of sensors including a pressure sensor 204, a temperature sensor 206, and a mass analyzer 208, a radiation sensor signal detector 210, an electromagnetic valve 212, a temperature control mechanism 214, a high-voltage power supply 320, and a hub 322 are provided for each Compton camera 200. On the other hand, an electromagnetic regulator branch valve 328 and a vacuum pump 324 are provided commonly for each Compton camera 200. In addition, a computer constituted by a controller 310, an input device 312, and an output device 314 is provided commonly for each Compton camera 200.

The controller 310 controls at least one of the electromagnetic valve 212, the electromagnetic regulator branch valve 328, and the temperature control mechanism 214 so as to set gases contained in the chamber 111 of each Compton camera 200 in different states.

Figure 10:
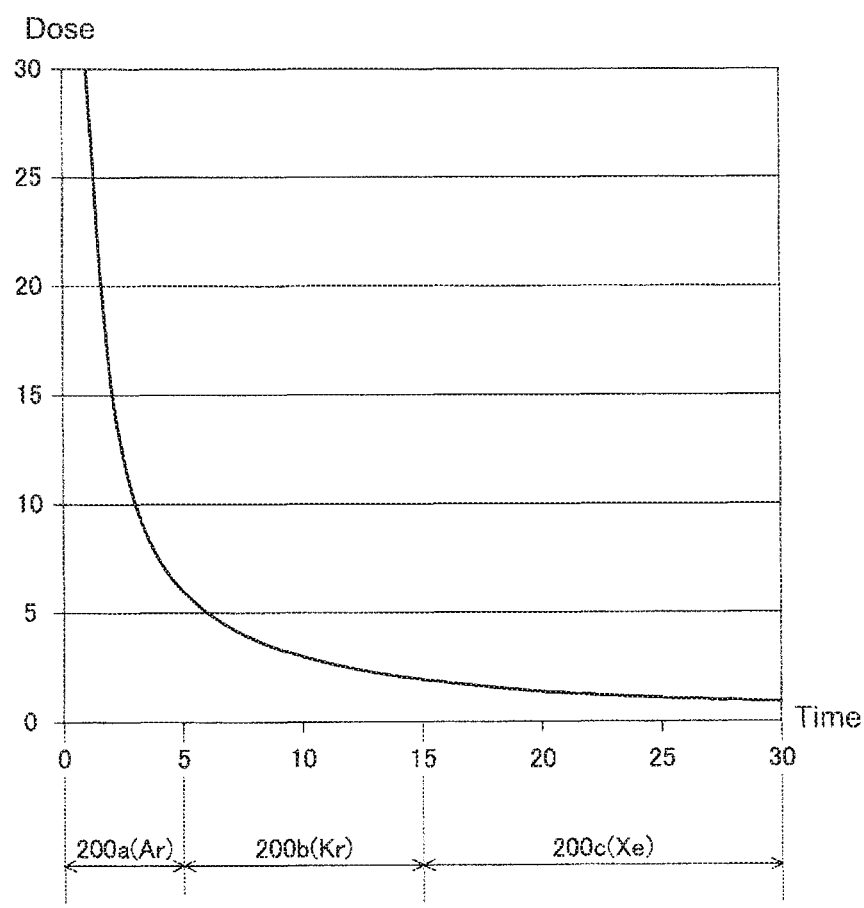
FIG. 10 is a graph showing a temporal change in the dose of radiation from a radiation source and control details concerning a gas composition by a gas state control unit.

FIG. 10 shows the relationship between a temporal change in the dose of radiation from a radiation source 450 and an example of control contents for gases by a gas state control unit 350. Note that in the case shown in FIG. 10, three Compton cameras 200a to 200c are incorporated in the nuclear medicine examination apparatus 300. Although not shown, the three gas cylinders 326 are prepared and respectively filled with a gas mixture containing argon and ethane at a ratio of 9:1, a gas mixture containing krypton and ethane at a ratio of 9:1, and a gas mixture containing xenon and ethane at a ratio of 9:1.

In the case shown in FIG. 10, first of all, the controller 310 controls the electromagnetic regulator branch valve 328 and the electromagnetic valves 212 of the Compton cameras 200a to 200c to fill the chamber 111 of the Compton camera 200a with a gas mixture containing argon and ethane at a ratio of 9:1, the chamber 111 of the Compton camera 200b with a gas mixture containing krypton and ethane at a ratio of 9:1, and the chamber 111 of the Compton camera 200c with a gas mixture containing xenon and ethane at a ratio of 9:1. The position of the radiation source 450 is specified while the Compton cameras 200a to 200c are sequentially switched with the lapse of time. More specifically, the position of the radiation source 450 is specified by the Compton camera 200a for the first 5 min, specified by the Compton camera 200b for the next 10 min, and specified by the Compton camera 200c afterward.

The reactive cross-sections of argon, krypton, and xenon increase in this order. As described above, using a gas with a large reactive cross-section increases the probability that two or more electron clouds will be simultaneously generated with an increase in drift time. Accordingly, using a gas with a large reactive cross-section (a gas mixture containing xenon and ethane at a ratio of 9:1) in a high-dose state will make it difficult to specify the position of the radiation source 450. Gradually increasing the reactive cross-section of the filled gas by switching the Compton cameras 200 with the lapse of time as described above makes it possible to specify the position of the radiation source 450 with a constant efficiency while preventing an excessive increase in the probability that two or more electron clouds will be simultaneously generated.

What is claimed is:

1. A nuclear medicine examination apparatus, comprising:
 a pixel-type radiation detection device configured to detect information of a charged particle generated by Compton scattering in a gas;
 one or a plurality of sensors configured to detect a physical amount of the gas; and
 a controller configured to control at least one of the physical amount and a composition of the gas based on output signals from the one or plurality of sensors.

2. The nuclear medicine examination apparatus according to claim 1, wherein
 the one or plurality of sensors include a pressure sensor configured to detect a pressure of the gas, and
 wherein control of at least one of the physical amount and composition of the gas by the controller includes controlling the pressure of the gas based on an output signal from the pressure sensor.

3. The nuclear medicine examination apparatus according to claim 1,
 wherein the one or plurality of sensors include a temperature sensor configured to detect a temperature of the gas.

4. The nuclear medicine examination apparatus according to claim 3,
 further comprising a temperature control mechanism configured to control the temperature of the gas,
 wherein control of the physical amount of the gas by the controller includes controlling the temperature of the gas by controlling the temperature control mechanism based on an output signal from the temperature sensor.

5. The nuclear medicine examination apparatus according to claim 1,
 wherein the one or plurality of sensors include a mass analyzer configured to detect a composition ratio of the gas.

6. The nuclear medicine examination apparatus according to claim 5, wherein control of the composition of the gas by the controller includes controlling the composition ratio of the gas based on an output signal from the mass analyzer.

7. The nuclear medicine examination apparatus according to claim 1,
further comprising a chamber into which the gas is introduced.

8. The nuclear medicine examination apparatus according to claim 1,
wherein the controller comprises:
a signal synchronization unit configured to associate an output signal from the one or plurality of sensors with a detection signal from the pixel-type radiation detection device,
a correction unit configured to correct the detection signal based on a corresponding output signal from the one or plurality of sensors, and
an image acquisition unit configured to acquire an image based on an indicated value corrected by the correction unit.

9. The nuclear medicine examination apparatus according to claim 1,
wherein the controller includes a driving condition control unit configured to control a driving condition for the pixel-type radiation detection device based on an output signal from the one or plurality of sensors.

10. The nuclear medicine examination apparatus according to claim 1,
wherein the pixel-type radiation detection device includes a first pixel-type radiation detection device configured to detect information of a charged particle generated by Compton scattering in a first gas and a second pixel-type radiation detection device configured to detect information of a charged particle generated by Compton scattering in a second gas different in composition from the first gas.

11. The nuclear medicine examination apparatus according to claim 1,
wherein the controller includes an information acquisition unit configured to acquire information concerning at least one of a nuclide and an initial dose of a radiation source, a measurement region, and an imaging angle and continuously or intermittently controls a physical amount of the gas based on information acquired by the information acquisition unit.

12. A nuclear medicine examination method of specifying a position of a radiation source emitted from a specimen by detecting a charged particle generated by Compton scattering in a gas,
the method comprising:
characterized by comprising adjusting a pressure of a gas that causes the Compton scattering when detecting radiation emitted from the radiation source.

13. The nuclear medicine examination method according to claim 12,
wherein a pressure of a gas generated by the Compton scattering is increased with a reduction in dose of radiation emitted from the radiation source.

14. The nuclear medicine examination method according to claim 12,
wherein a pressure of a gas generated by the Compton scattering is increased with a lapse of time.

15. The nuclear medicine examination method according to claim 12,
wherein control is performed to keep a temperature of a gas generated by the Compton scattering constant.

16. The nuclear medicine examination method according to claim 12,
wherein control is performed to keep a composition ratio of a gas generated by the Compton scattering constant.

17. A nuclear medicine examination method of specifying a position of a radiation source emitted from a specimen by detecting a charged particle generated by Compton scattering in a gas,
the method comprising:
characterized by comprising adjusting a type of gas that causes the Compton scattering when detecting radiation emitted from the radiation source.

18. The nuclear medicine examination method according to claim 17,
wherein a gas that causes the Compton scattering comprises a gas mixture of a rare gas and a gas having a quenching effect, and the type of rare gas is adjusted.

19. The nuclear medicine examination method according to claim 17,
wherein the gas that causes the Compton scattering comprises a gas mixture of a rare gas and a gas having a quenching effect, and
wherein the rare gas is changed to a rare gas having a larger reactive cross-section with a reduction in dose of radiation emitted from the radiation source.

20. The nuclear medicine examination method according to claim 17,
wherein the gas that causes the Compton scattering comprises a gas mixture of a rare gas and a gas having a quenching effect, and
wherein the rare gas is changed in an order of argon, krypton, and xenon with a reduction in dose of radiation emitted from the radiation source.

* * * * *